United States Patent [19]

Tomasi

[11] Patent Number: 5,313,960
[45] Date of Patent: May 24, 1994

[54] APPARATUS AND METHOD FOR REDUCING SNORING AND METHOD OF MAKING SAME

[75] Inventor: Barbara R. Tomasi, Hailey, Id.

[73] Assignee: Marc S. Bernstein, Los Angeles, Calif.

[21] Appl. No.: 971,336

[22] Filed: Nov. 4, 1992

[51] Int. Cl.$^5$ .................. A61F 5/56; A61C 5/14
[52] U.S. Cl. .................. 128/848; 128/859; 128/861; 128/862
[58] Field of Search .............. 128/62 R, 845, 848, 128/859–862; 433/6, 24, 42, 44, 46

[56] References Cited

U.S. PATENT DOCUMENTS

| | | | |
|---|---|---|---|
| D. 302,036 | 7/1989 | George | D24/34 |
| 587,358 | 8/1897 | Anderson . | |
| 746,869 | 12/1903 | Moulton . | |
| 900,541 | 10/1908 | Hol/mes | 433/43 |
| 1,674,336 | 6/1928 | King . | |
| 2,424,533 | 7/1947 | Faires | 128/136 |
| 2,574,623 | 11/1951 | Clyde | 128/136 |
| 2,627,268 | 2/1953 | Leppich | 128/136 |
| 2,706,006 | 3/1955 | Cettel et al. | 128/136 |
| 2,827,899 | 3/1958 | Altieri | 128/862 |
| 2,833,278 | 5/1958 | Ross | 128/862 |
| 3,132,647 | 5/1964 | Corniello | 128/136 |
| 3,236,235 | 2/1966 | Jacobs | 128/862 |
| 3,312,218 | 4/1967 | Jacobs | 128/862 |
| 3,434,470 | 3/1969 | Strickland | 128/136 |
| 3,478,742 | 11/1969 | Bohlmann | 128/172.1 |
| 3,536,069 | 10/1970 | Gores | 128/861 |
| 4,161,067 | 7/1979 | Bekey | 433/42 |
| 4,169,473 | 10/1979 | Samelson | 128/136 |
| 4,173,219 | 11/1979 | Lentine | 128/861 |
| 4,196,724 | 4/1980 | Wirt et al. | 128/136 |
| 4,304,227 | 12/1981 | Samelson | 128/136 |
| 4,715,368 | 12/1987 | George | 128/136 |
| 4,760,248 | 6/1990 | Shapiro | 128/200.24 |
| 4,901,737 | 2/1990 | Toone | 128/848 |
| 4,986,283 | 1/1991 | Tepper | 128/859 |
| 5,003,994 | 4/1991 | Cook | 128/848 |
| 5,056,534 | 10/1991 | Wright | 128/848 |
| 5,082,007 | 1/1992 | Adell | 128/859 |
| 5,117,816 | 6/1992 | Shapiro | 128/861 |

OTHER PUBLICATIONS

A. Jönsson et al., "Evaluation of a New Anti-Snoring Device", ORL 1989; 51:311–316.
Brochure entitled "The Tepper Oral Proprioceptive Stimulator"; Dr. Harry W. Tepper, Custom-Pallisades Dental Laboratory, Newhall, Calif. (no date).

(List continued on next page.)

Primary Examiner—Michael A. Brown
Attorney, Agent, or Firm—Lyon & Lyon

[57] ABSTRACT

An oral appliance and method for reducing snoring including upper and lower mouthpiece portion, each of which having a rigid structural core and a relatively soft outer portion which may be conformed to fit the upper teeth of the user. The upper and lower mouthpiece portions are first mounted on a holder with the upper mouthpiece portion positioned forward a desired offset amount from the lower mouthpiece portion (preferably about 3.0 mm). The entire assembly is then heated and the outer soft material of the upper and lower mouthpiece portions softens and may be placed in the mouth to permit the mouthpiece portions to be conformed to the upper and lower teeth. Once the upper and lower mouthpiece portions have been properly fitted, the assembly is removed from the mouth and allowed to set into a permanent state. The upper and lower mouthpiece portions are then removed from the holder and attached directly to one another without any offset therebetween forming the full mouthpiece. The result is that when reinserted into the mouth, the mandible is adjusted forward by an amount corresponding to the previous offset.

20 Claims, 10 Drawing Sheets

OTHER PUBLICATIONS

Glenn T. Clark, DDS, "OSA and Dental Appliances", DA Journal, Oct. 1988, pp. 26–31).

Paul E. Bonham et al., "The Effect of Modified Functional Appliance on Obstructive Sleep Apnea", Am. J. Orthod. Dentofac. Orthop., Nov. 1988, pp. 384–392.

Wolfgang W. Schmidt-Nowara et al., "Treatment of Snoring and Obstructive Sleep Apnea with a Dental Orthosis", CHEST/99/6/Jun., 1991, pp. 1378–1385.

A. George Wagner et al., "An Intraoral Device to Prevent Snoring", General Dentistry/May–Jun. 1987, pp. 212–213.

Charles F. Samelson, MD, "The Role of Tongue Retaining Device in Treatment of Snoring and Obstructive Sleep Apnea", CDS Review, Oct. 1988, pp. 44–47.

Brochure entitled "Introducing Snore-No-More" Dentec, 4 pages, (no date).

Brochure entitled "When Snoring Isn't a Laughing Matter", Dental Sleep Disorder Prevention, 2 pages (1991) and one page brochure entitled The Snore Guard Device-Effective Treatment for Snorinng (no date).

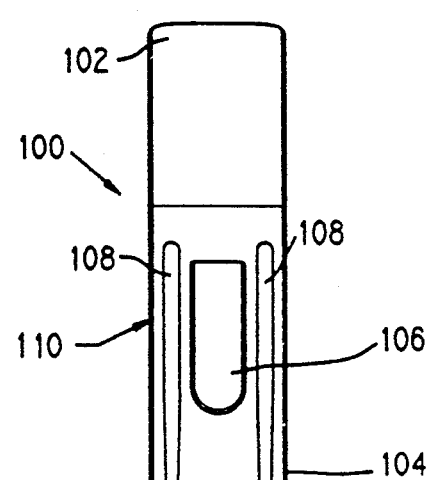
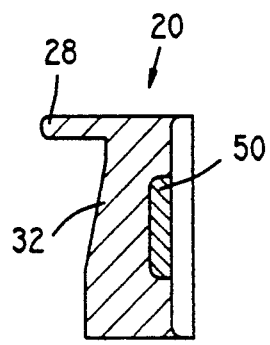
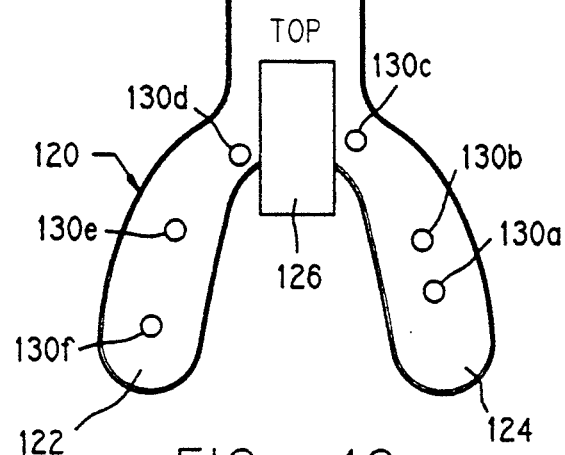
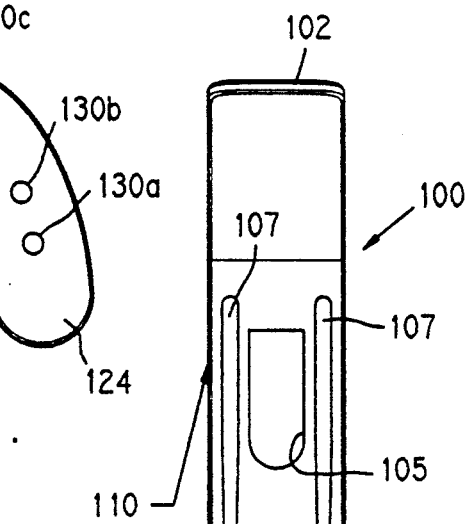
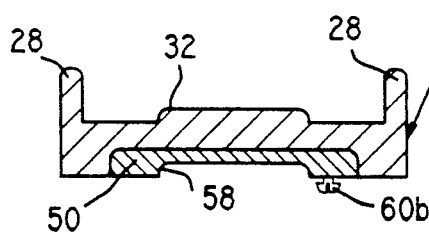
FIG. 16.
FIG. 17.
FIG. 18.
FIG. 19.

APPARATUS AND METHOD FOR REDUCING SNORING AND METHOD OF MAKING SAME

BACKGROUND OF THE INVENTION

The field of the present invention relates to devices and methods for reducing snoring. According to the literature, a large portion of the population experiences difficulties in breathing when sleeping resulting primarily in snoring or sleep apnea. There have been many methods and devices proposed or attempted to reduce or prevent snoring. Many of the devices are highly uncomfortable and most of the devices include other disadvantages such as high expense, complicated fitting procedures, and inaccurate adjustment mechanism.

The sounds associated with snoring are generally produced by the vibration of soft tissue as air passes through the rear portion of the mouth.

The present inventor has recognized that much of the noise of snoring is accentuated by retrusion of the lower jaw (the mandible) relative to the upper teeth. Retrusion is the tendency of the lower jaw to slump rearwardly, particularly when the person is sleeping on his/her back thereby causing narrowing of the posterior pharyngeal space and restriction of air flow through the back of the mouth. Such restriction of the airway may increase the sound of snoring. Further restriction may be caused by rearward retrusion of the tongue. The present inventor has recognized that certain devices are designed to prevent retrusion of the lower jaw, i.e., rearward movement of the lower jaw from the at rest and intercuspal (ICP) positions. The present inventor, however, has also recognized that protrusion or forward movement of the lower jaw from the relaxed and ICP stage is desirable to prevent or reduce the noise of snoring.

SUMMARY OF THE INVENTION

The present invention is directed to a method and oral appliance for reducing snoring. In a preferred embodiment, the present invention includes an upper mouthpiece portion having a rigid structural core and a relatively soft outer portion which may be conformed to fit the upper teeth of the user, a lower mouthpiece portion also having a rigid structural core and a relatively soft outer portion which may be fitted to the lower teeth of the user. The upper and lower mouthpiece portions are first mounted on a holder with the upper mouthpiece portion positioned forward a desired offset amount from the lower mouthpiece portion (preferably about 3.0 mm). The entire assembly is then heated and the outer soft material of the upper and lower mouthpiece portions softens and may be placed in the mouth to permit the mouthpiece portions to be conformed to the maxillary and the mandibular teeth. Once the upper and lower mouthpiece portions have been properly fitted, the assembly is removed from the mouth and allowed to cool into a permanent state. The upper and lower mouthpiece portions are then removed from the holder and attached directly to one another without any offset therebetween. The result is that when reinserted into the mouth, the lower jaw or mandible is adjusted forward the offset amount corresponding to the previous offset.

BRIEF DESCRIPTION OF THE DRAWINGS

FIGS. 16 is a cross-sectional view of FIG. 10 taken along line 16—16;

FIG. 17 is a cross-sectional view of FIG. 10 taken along line 17—17;

FIG. 18 is a top plan view of the holder element of FIG. 1;

FIG. 19 is a bottom plan view of the holder element of FIG. 18;

FIG. 21 is a detailed view of the holder leg section of FIG. 21;

DETAILED DESCRIPTION OF THE PREFERRED EMBODIMENTS

The preferred embodiments will now be described with reference to the drawings. To facilitate the description, numerals designating an element in one figure will represent the same element in any other figure.

Figure 1:
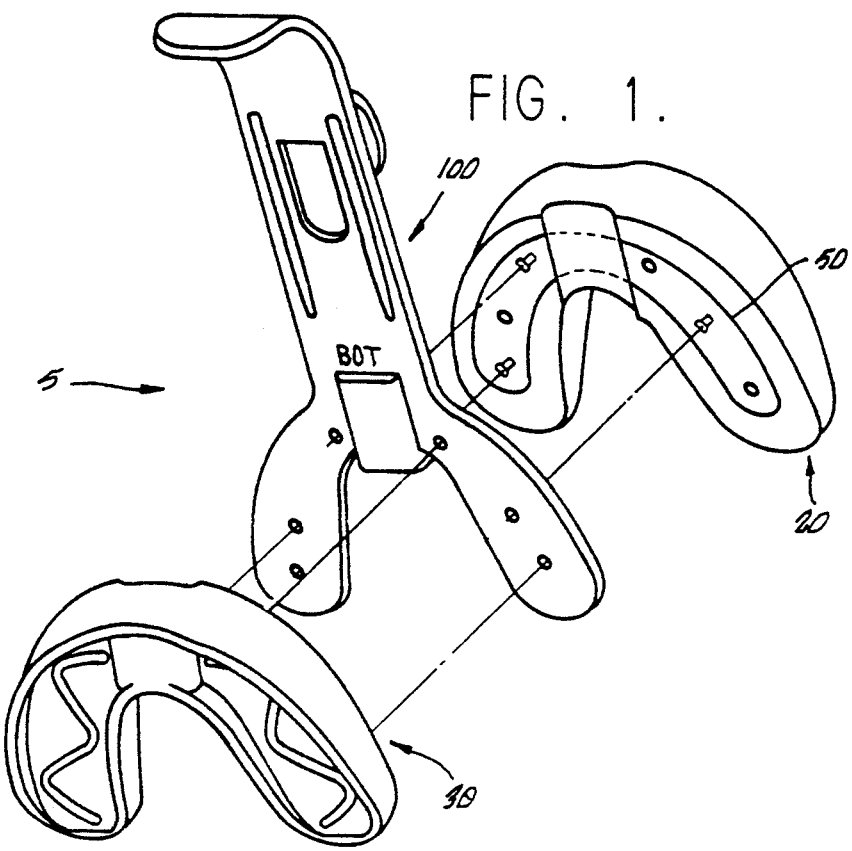
FIG. 1 is an exploded perspective view of the oral appliance and holder according to the preferred embodiment of the present invention.

FIG. 1 is a perspective exploded view of the antisnore system 5 according to the present invention. The system 5 includes an upper impression tray or mouthpiece portion 20, a lower impression tray or mouthpiece portion 30, and a holder or applicator piece 100. The upper impression tray portion 20 and the lower impression tray portion 30 are preferably of identical configuration and are detachably connectable to the holder 100 on opposite sides thereof. The upper and lower impression tray portions 20, 30 being of identical configuration, requires that only a single mold and/or manufacturing process need be employed to make the two parts, thereby reducing manufacturing costs.

Since the upper and lower impression tray portions 20, 30 are identical, only the upper impression tray portion 20 will now be described, but the following description also applies to the lower impression tray portion 30. The upper impression tray portion 20 includes an inner core piece 50 being constructed from a stiff plastic such as ABS or some other stiff plastic such as acrylic, for example, which is FDA approved for intraoral use. The core piece 50 is generally surrounded by relatively soft 0 flexible covering of a plastic material such as Elvax ® which is heat deformable, such as by placing the element in heated water or some other suitable heating method, and may then be molded to fit the upper teeth (or lower teeth if the lower mouthpiece portion 30 is being fitted) of the person's mouth. As will be described below, in the preferred fitting method, the upper and lower impression tray portions 20, 30 will be connected to the applicator 100 when heated and fitted simultaneously. Once the portion is removed from the person's mouth, it is allowed to cool and will retain its shape conformed to the particular user's mouth thereby taking a functional impression in the Elvax. ®

Figure 2:
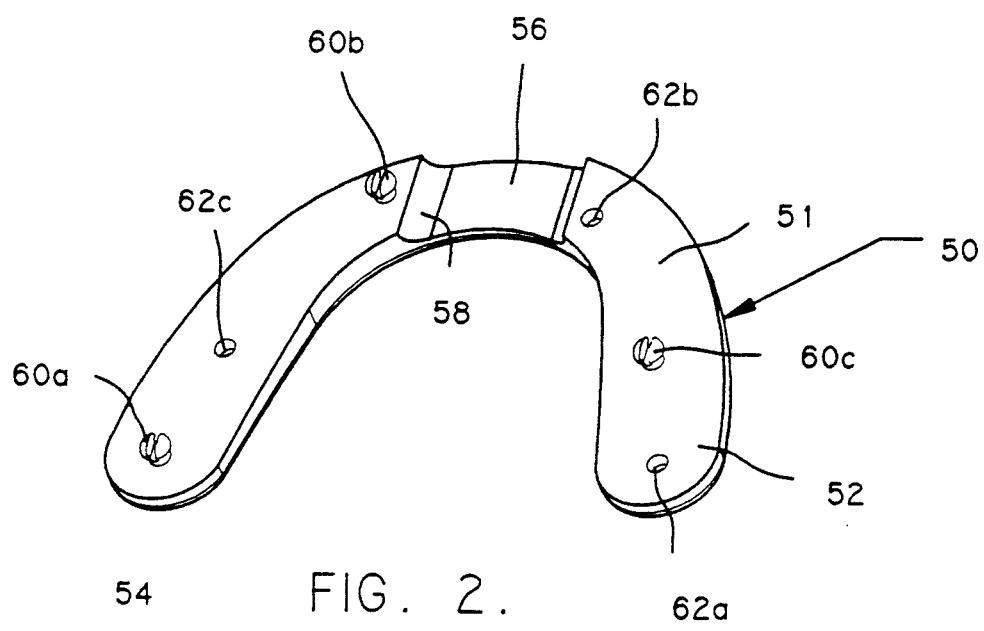
FIG. 2 is a perspective view of the stiff core piece of the mouthpiece portion of the oral appliance of FIG. 1.
Figure 3:
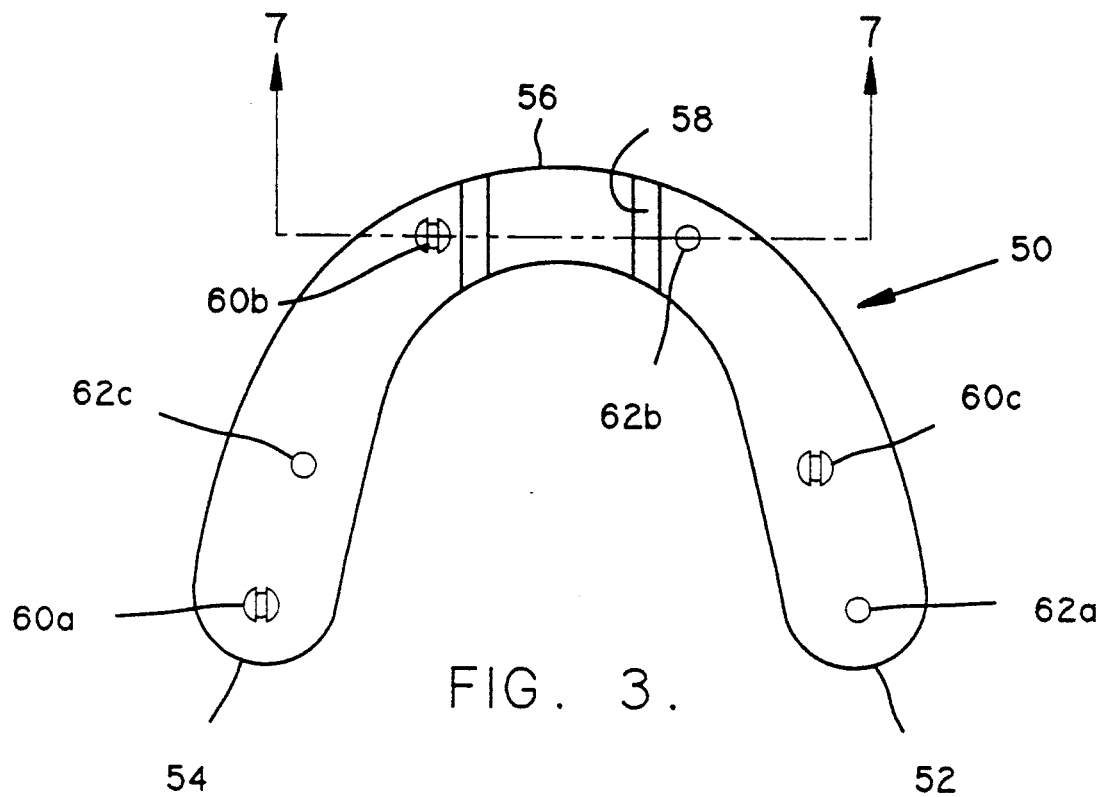
FIG. 3 is a top plan view of the core piece of FIG. 2.
Figure 4:
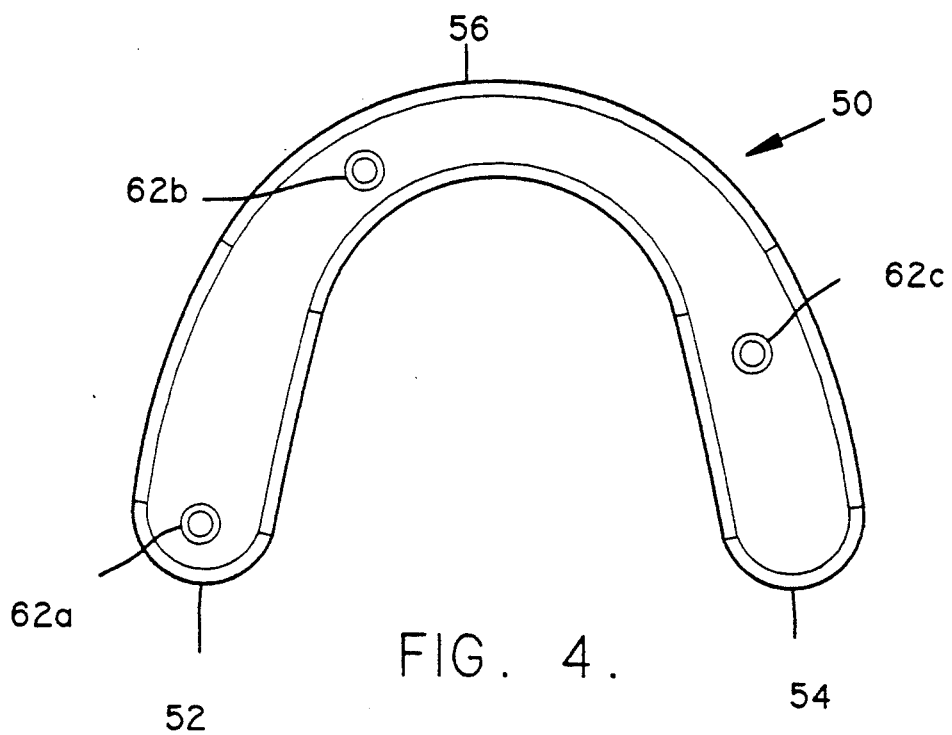
FIG. 4 is a bottom plan view of the core piece of FIG. 2.

Referring to FIGS. 2-9, the inner core piece 50 is generally a horseshoe or U-shaped member having a plurality of connecting elements on what will be defined as the inner side 51 thereof which faces and connects to the applicator 100, as best shown in FIG. 2. The connecting elements comprise protruding connectors 60a, 60b, and 60c alternatively spaced about the core piece 50 with holes 62a, 62b, and 62c, as best shown in FIG. 3. It should be noted that a protruding connector element such as 60a has a corresponding symmetrically placed hole 62a on the other side of the U-shaped core piece 50. As will be shown later, a core piece of identical configuration (such as contained within lower mouthpiece portion 30) will snap fit and attach to the upper core piece 50, the protruding connectors 60a-c in upper core piece 50 snap fitting into the holes of the core piece of lower mouthpiece portion 30 and corresponding protruding connectors of the core piece in lower mouthpiece 30 will snap fit into the holes 62a-c of upper core piece 50.

The upper core piece 50 also includes a front portion 56. The core piece 50 has a forward indentation 58 which, as will be discussed later, provides a breathing airway in the front face of an assembled unit.

Figure 5:
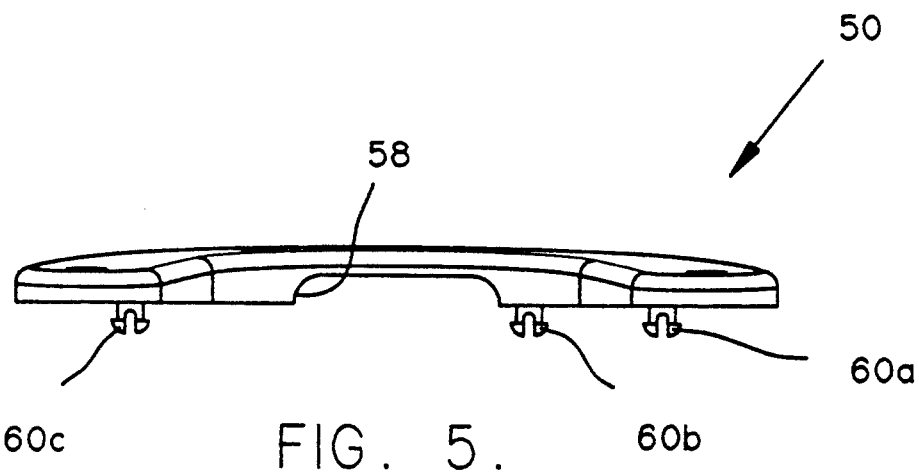
FIG. 5 is a rear view of the core piece of FIG. 2.
Figure 6:
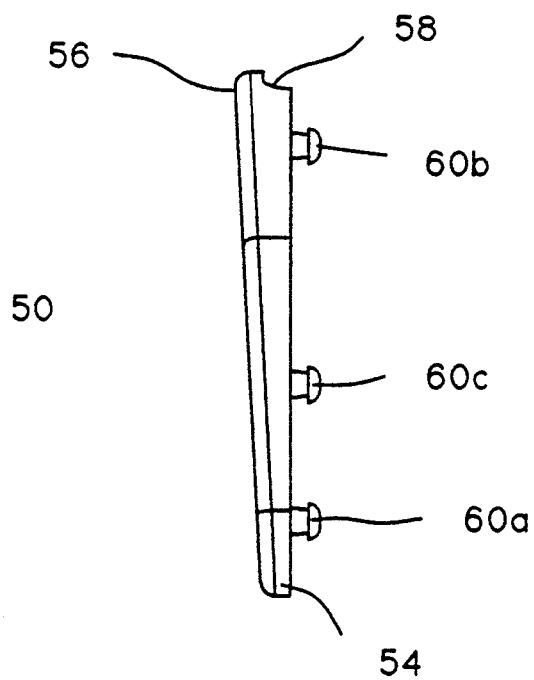
FIG. 6 is a side view of the core piece of FIG. 2.
Figure 7:
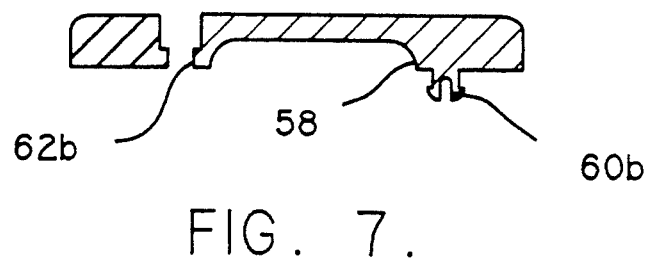
FIG. 7 is a cross-sectional view of the core piece of FIG. 3 taken along line 7—7.
Figure 8:
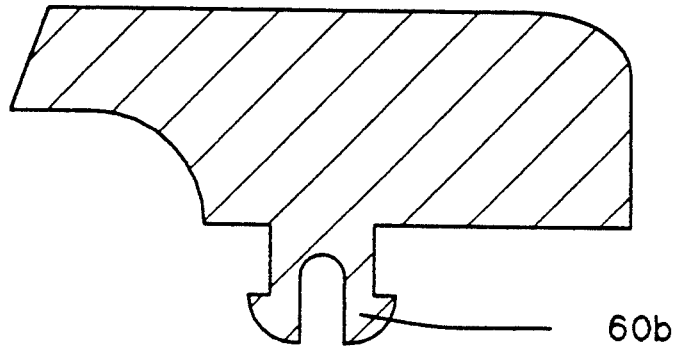
FIG. 8 is a detailed view of the protruding connecting element of FIG. 7.
Figure 9:
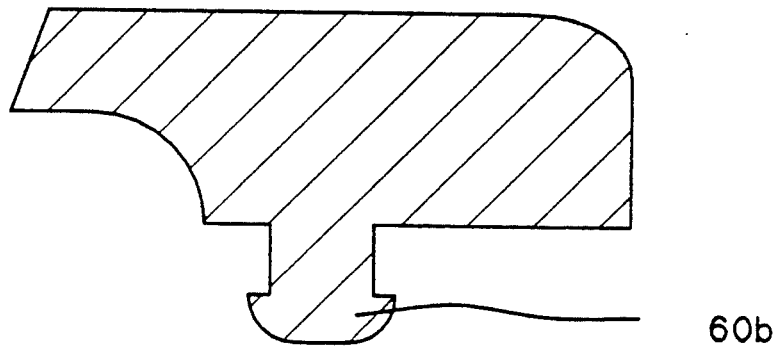
FIG. 9 is a detailed view of an alternate preferred design for a protruding connecting element.
Figure 10:
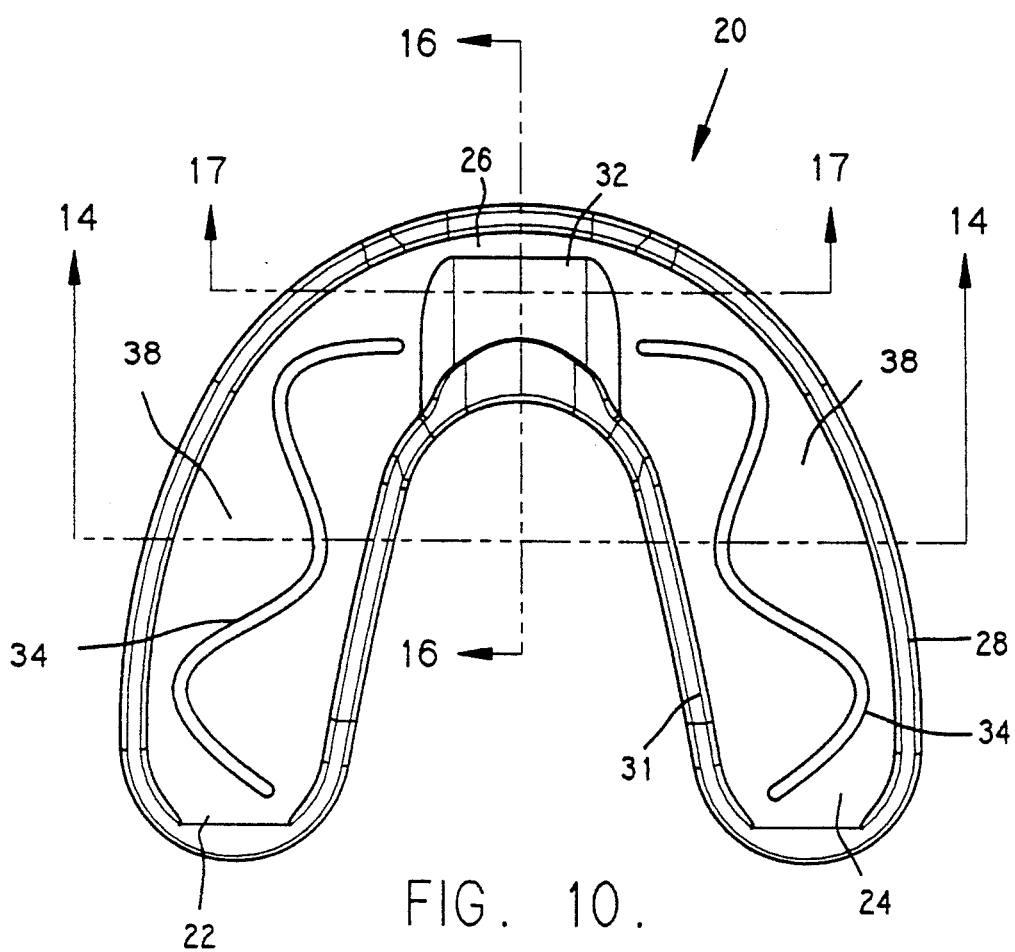
FIG. 10 is a top elevation view of a mouthpiece portion of FIG. 1.
Figure 11:
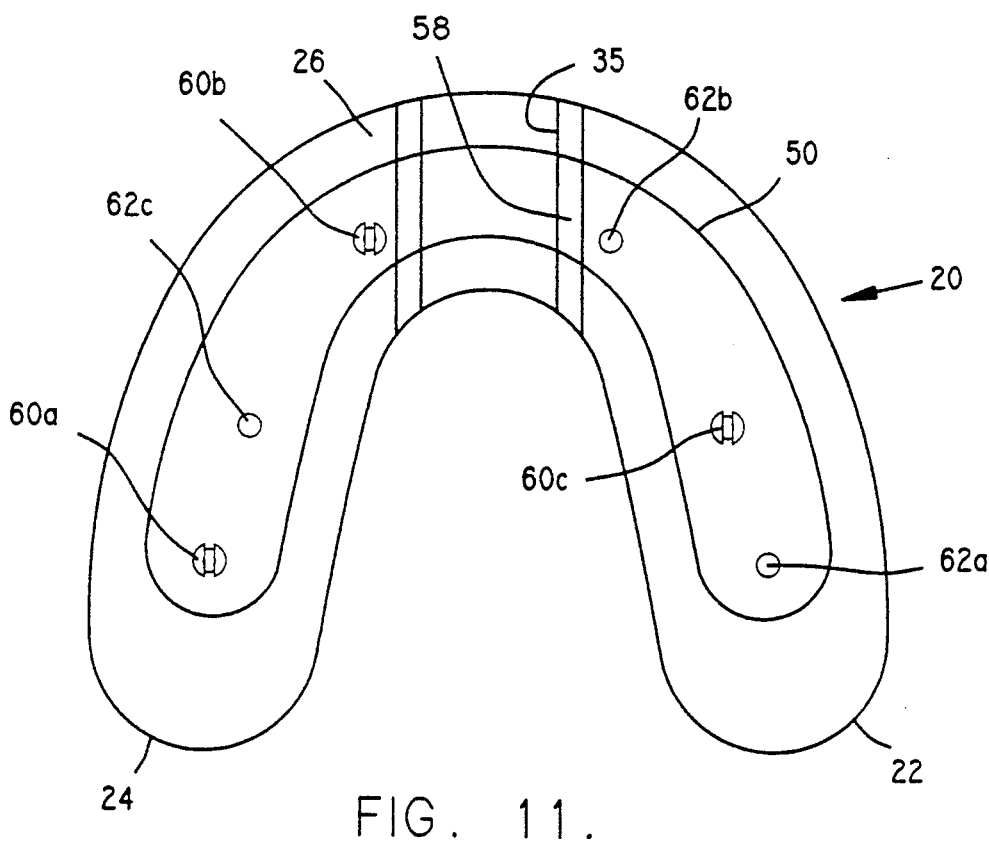
FIG. 11 is a bottom plan view of the mouthpiece element of FIG. 10.
Figure 12:
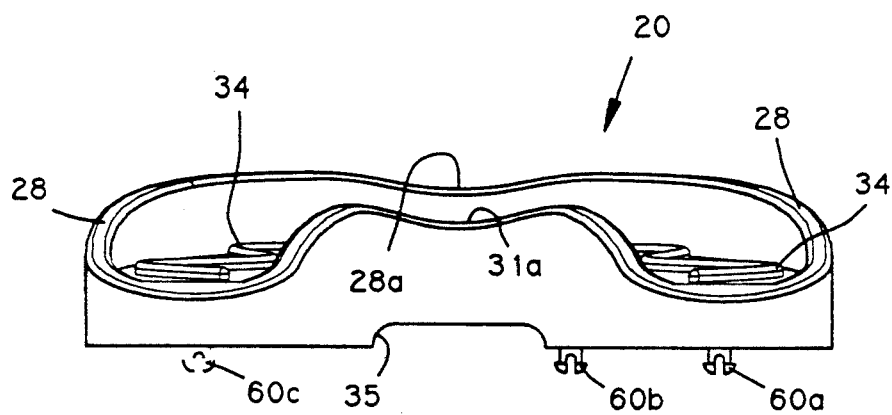
FIG. 12 is a rear view of the mouthpiece element of FIG. 10.
Figure 13:
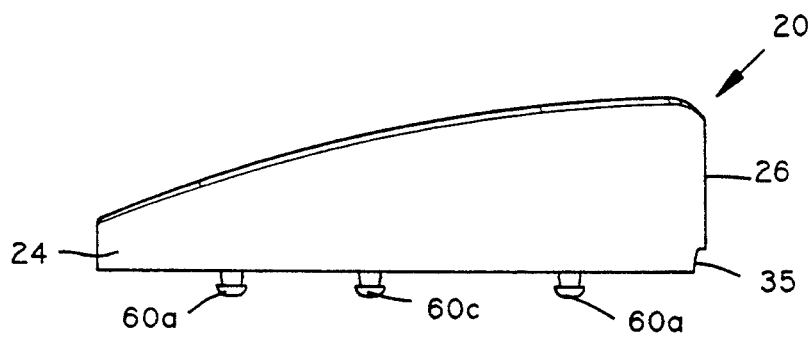
FIG. 13 is a side elevation view of the mouthpiece element of FIG. 10.
Figure 14:
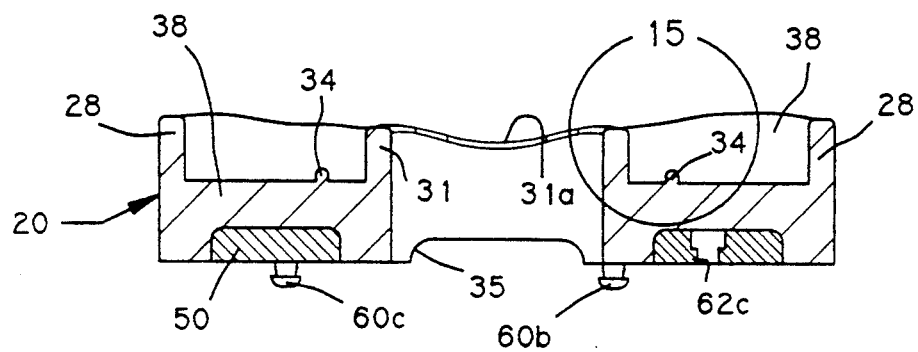
FIG. 14 is a cross-sectional view of FIG. 10 taken along line 14—14.
Figure 15:
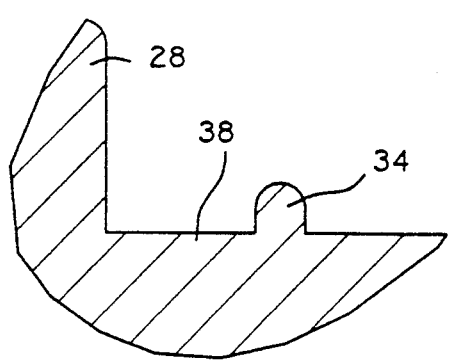
FIG. 15 is a detailed view of a channel section of FIG. 14.
Figure 20:
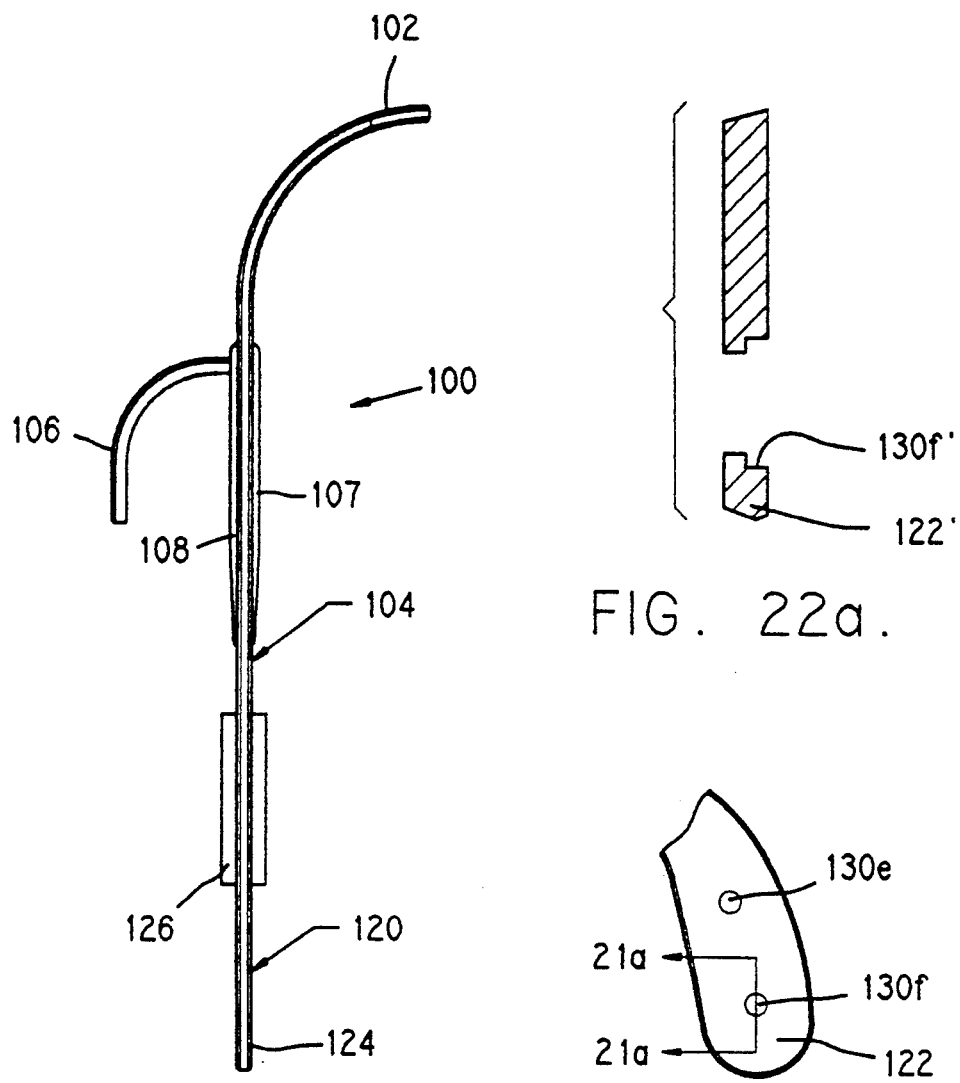
FIG. 20 is a side elevation view of the holder element of FIG. 18.
Figure 22A:
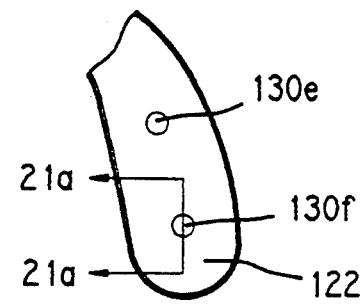
FIG. 22A is a cross-sectional view of FIG. 21 taken along line 22A—22A.
Figure 21A:
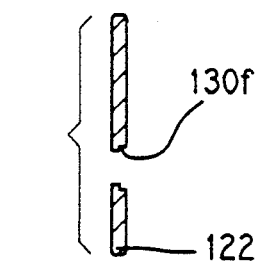
FIG. 21A is a cross-sectional view of FIG. 21 taken along line 21A—21A.
Figure 22:
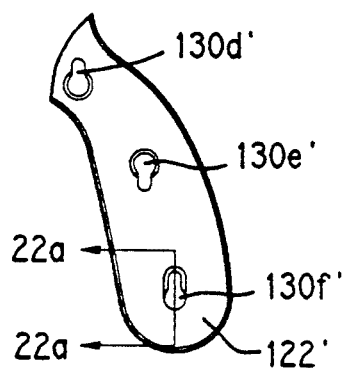
FIG. 22 illustrates an alternate embodiment for the holder leg section.

As best illustrated in FIGS. 2, 5 and 6, the core piece 50 is ramped in thickness, having a smaller thickness (about 2 mm) at its leg portions 52, 54 and a larger thickness (about 4 mm) at the front face 56. When positioned in the mouth, the U-shaped core piece 50 has its leg portions 52, 54 toward the back of the mouth, the posterior region, and the front face 56 toward the front of the mouth, the anterior region. The ramp or angle of the core piece 50 is designed to account for pivoting action of the human jaw. The human jaw pivots about an axis located at the temporomandibular joint (TMJ) approximately 1 cm anterior to the tragus of the ear. The result is that when the jaw is opened, the front of the mouth, which is farther away from the pivot point, is opened to a greater degree than the rear portion of the mouth. Studies have shown this 4 mm/8 mm total ramp amount (from the two mouthpiece portions 20, 30) to be generally acceptable for the TMJ, the ramped construction accommodating this oral geometry possessed by the human mouth.

The assembled mouthpiece portion 20 is illustrated in FIGS. 1 and 10-17. The mouthpiece portion 20 is generally an arch or U-shaped and comprises leg portions 22, 24 and a central section 26. The outer covering material is preferably made from a silicon material, such as Elvax ®, which is heat conformable and FDA approved and medically accepted for intraoral use. The mouthpiece portion 20 includes an outer wall portion 28 and an inner wall portion 31 which form a cup or channel 38 for the user's teeth, the outer wall portion 28 being positionable in the space between the user's teeth and gum and the user's lip. The inner wall portion 31 is then positionable against the inside surface of the user's teeth and gums. The outer wall portion 28 decreases in height from the front area 26 to the leg portions 22, 24. The outer wall portion 28 also has a lowered height wall portion 28a in the center of the front section 26. Similarly, the inner wall portion 31 has an indented or lowered wall height section 31a at the forward portion of the mouth to accommodate an anatomical structure and the inner wall portion 31 decreases in height toward the rear of the mouthpiece 20.

The tooth-side surface of the mouthpiece portion includes a channel 35 which cooperates with the channel 58 of the core piece 50 for providing an airway to be described later.

The mouthpiece portion is provided with sufficient thickness of Elvax ® on the tooth side of the core piece 50 to allow the desired forming of the material around the teeth of each arch thereby taking a impression. The pliable portion is constructed from a material having sufficient softness for desired comfort but sufficient stiffness for tooth retention capability. A front tooth guide ramp 32 is preferably provided in the front section 26 of the mouthpiece portion 20. The desired position of the front teeth is forward within the channel 38 of the impression tray 20. The guide ramp 32 is a forwardly and downwardly sloping raised section which helps guide the front (anterior) teeth forward as much as possible, to the proper position in the tooth channel 38 during the fitting process to allow proper seating of the teeth in the channel 38.

The tooth channel 38 may be provided with raised guides or ridges 34, 34. These proprioceptive ridges 34 are raised tongue portions positioned about the tooth channel 38 which serve to provide some slight proprioception and a minimal guidance to the teeth during the fitting process. Such raised ridges may be of any suitable geometry, continuous or discontinuous, straight or curved, but merely provide for early contacting of the teeth on a portion of the tooth channel 38 during the fitting process.

FIGS. 18-22 illustrate the holder 100 being comprised of an upper handle portion 110 and a lower holder portion 120. The handle portion 110 includes a curved end portion 102 which curves downward in the direction toward what we refer to as the bottom of the holder 100. The holder 100 is preferably of one piece construction molded from a stiff plastic such as acrylic which does not deform under the temperatures experienced during the heat fitting process. The lower portion 120 is generally of U-shape corresponding to the mouthpiece portion 20 previously described. The lower portion 120 includes leg sections 122, 124 and a plurality of holes 130a, 130b, 130c, 130d, 130e, 130f corresponding to the number of protruding connectors on the upper and lower mouthpiece portions 20, 30.

The lower holder section 120 also includes a spacer bar 126 positioned at an upper section of the lower portion 120 protruding into the "U" of the lower section 120. When the upper and lower mouthpiece portions 20, 30 are attached to the holder 100, the spacer 126 fills the channel space 35, 58 thereby maintaining the integrity of the channel 58 during the forming process. The handle portion 104 of the holder 100 includes an extending hook portion 106 which may be used to support the holder on the side of the heating unit (e.g. a pot of heated water) during the heating step. If desired, the handle 100 may include an outwardly extending diagonal prop or spacer, positioned for example between the hook portion 106 and the holder portion 120, to maintain spacing between the appliance and the side of the heating unit. The handle section 110 includes a hole 105 corresponding to the hook portion 106. Stiffening bars 107, 107 and 108, 108 are positioned on either side of the hole 105 both on the top side and on the bottom side of the handle portion 110 to provide additional stiffening or support for the handle in the region of the hole 105.

A specialized heating unit may be employed eliminating the need for the handle portion 110, but the handle portion 110 allows for convenient handling and manipulation of the appliance during the entire fitting process.

Figures 23, 24, 25:
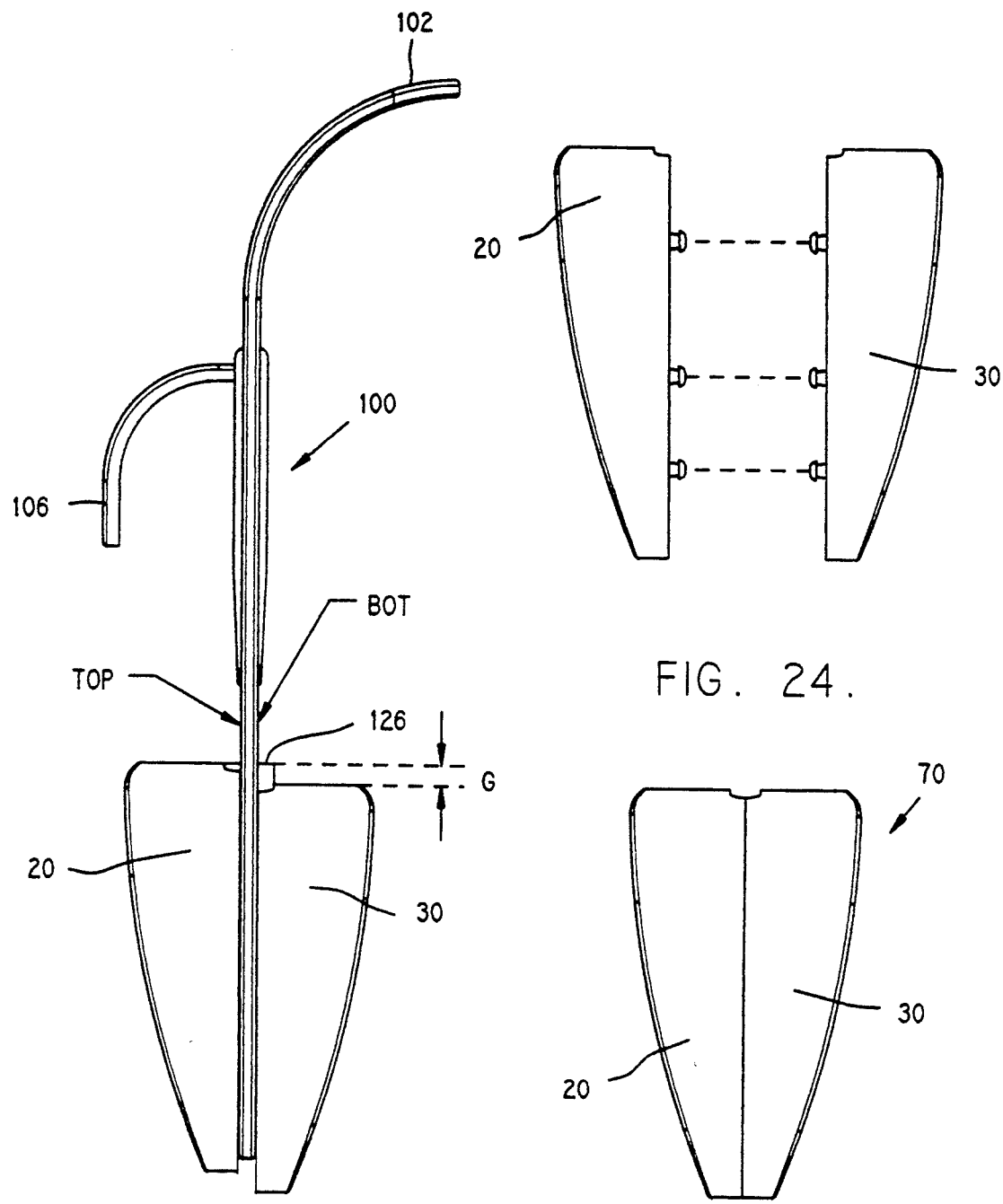
FIG. 23 is a side elevation view of an assembled unit ready for the fitting process.
FIG. 24 is a side elevation view of the upper and lower mouthpiece portions detached from the handle of FIG. 23 and showing alignment for attachment.
FIG. 25 is a side elevation view of a final assembled oral appliance.

As illustrated in FIGS. 18-19 and 23, the holder 100 includes side designations TOP corresponding to the top of the holder 100 and BOT corresponding to the bottom of the holder 100. Other suitable designations such as "UP" and "DOWN", "THIS SIDE UP", a suitable designation in any language, or suitable universal symbols may be employed. The purpose of the designation is functional to assure that the assembled unit is oriented correctly during the fitting process. As viewed in FIG. 23, when installed on the holder 100, the upper and lower mouthpiece portions 20, 30 are offset or spaced by gap or offset "G" which corresponds to the desired protrusion adjustment. It is important that the upper mouthpiece portion indicated by the "TOP" designation on the holder 100 be fitted to the upper teeth or maxilla while the lower mouthpiece portion 30, as indicated by the "BOT" designation on the holder 100, be fitted to the lower teeth or lower mandible portion of the mouth.

The downwardly curved end portion 102 of the handle 100 provides for convenient manipulation. The curved end portion 102 also helps to identify the proper orientation of the holder 100 and assembled mouthpiece portions 20, 30 during the fitting process.

In a preferred fitting process, an assembled unit, as illustrated in FIG. 23, with the upper and lower mouthpiece portions 20, 30 installed on the handle 100, is placed in hot water which has been boiled and removed from the heat, for approximately 40 to 60 seconds. The heat of the water softens the pliable plastic coverings of the upper and lower mouthpiece portions 20, 30 making them reasonably pliable. After removal from the water, the mouthpiece portions may be momentarily rinsed in cold water to lower the temperature of the material so that it may be quickly inserted into the mouth to provide the desired fit. Following the designations "TOP" and "BOT", the user orients the upper mouthpiece portion for the upper portion of the mouth with the curved handle portion 102 points downward. As the person bites down on the mouthpiece portions 20, 30, (a) the guide ramps 32 urge the front teeth forward to a desired position in the tooth channel 38, (b) the soft and pliable plastic material conforms to the teeth and the gums and (c) the wall portions are manipulated with the fingers and tongue of the user to achieve the desired fit. The spacer 126 maintains the integrity of the channel 58 in the respective mouthpiece portions 20, 30. The entire unit is then removed from the mouth and allowed to cool. Next the upper and lower mouthpiece portions ar removed from the holder 100 and reassembled face-to-face as illustrated in FIG. 24 without the offset G of FIG. 23. The holder 100 may then be discarded.

Figure 26:
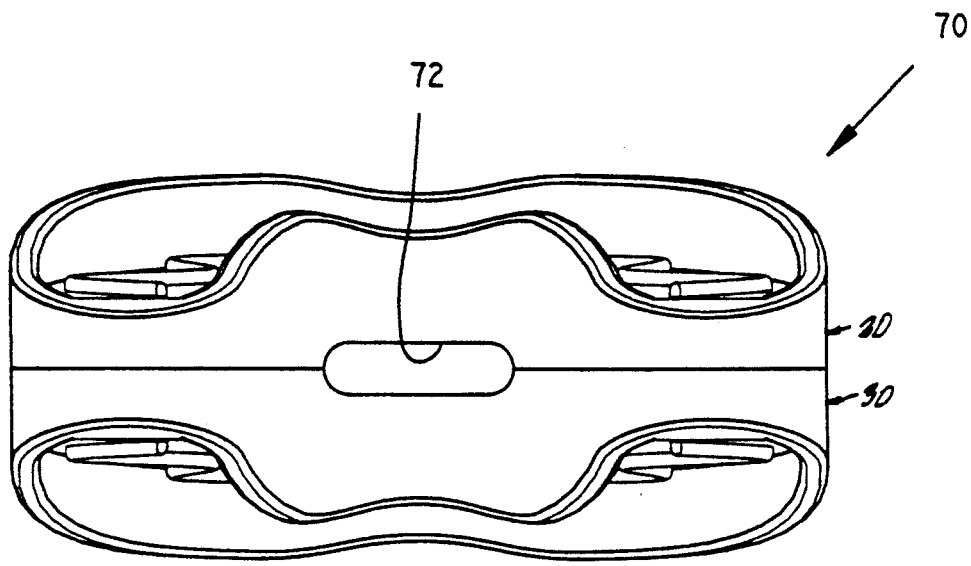
FIG. 26 is a rear elevation view of the assembled oral appliance of FIG. 25.
Figure 27:
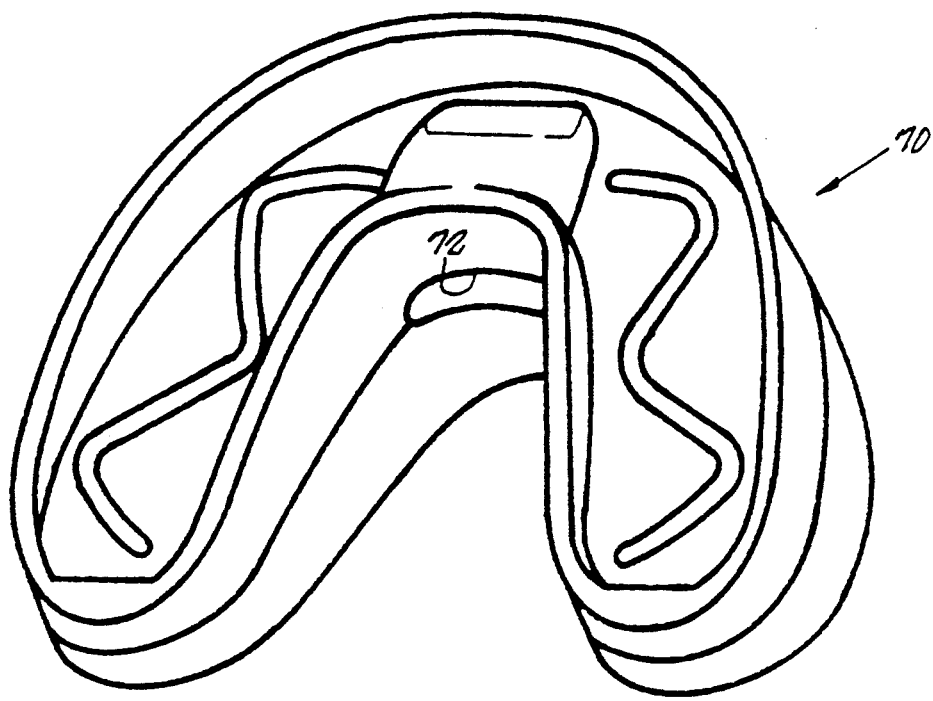
FIG. 27 is a perspective view of the assembled oral appliance.

As best shown in FIGS. 25-27, the assembled and fitted mouthpiece 70 is comprised of the upper mouthpiece portion 20 attached to the lower mouthpiece portion 30. An internal airway channel 72 is formed between the upper and lower mouthpiece portions 20, 30. When inserted into the mouth, the mouthpiece 70 acts to not only prevent retrusion or rearward movement of the lower jaw by holding the lower jaw in position with the upper jaw, but the lower jaw is advanced forward 3.0 mm because of the corresponding offset G (see FIG. 23) introduced during the fitting process.

The present inventor has recognized that by controlling the relative position of the lower jaw to the upper jaw, snoring can be reduced or eliminated for many individuals. For most individuals, the usual bite position (the intercuspal position) is such that the front (anterior) lower teeth are slightly in arrears of the front (anterior) teeth of the upper jaw (Class I or minimal Class II position). Snoring may be caused by or aggravated by retrusion or rearward movement of the lower jaw during sleep. By preventing retrusion with the appliance 70, or most desirably by creation a slight protrusion, i.e., advancing the lower jaw forward the desired amount, slumping of soft tissue including the tongue may be reduced. The tendencies to snore may thus be reduced or eliminated.

The present inventor has found that an advance or offset of 3.0 mm is an effective amount of adjustment for many or most individuals. This 3.0 mm adjustment is selected as an average protrusion readily tolerable by the average adult no matter of what size. It is conceivable that there could be different appliance sizes or ranges of appliance sizes to accommodate persons of different mouth sizes. Furthermore, the device could be readily altered, such as by providing an alternate handle with different hole positions in order to provide a different offset (i.e., the gap G) suitable for different persons. It may be desirable, for example, for a particularly large man to have a 4.0 mm advance (or any desired advance) of his lower jaw in order to reduce his snoring. As such, the appliance may be supplied in a range of sizes (e.g., small, medium, large) and/or offsets (e.g., 0-4.0 mm) to accommodate users of different mouth sizes and different lower mandible adjustment requirements. In general, the preferred offset range is from 2.0 mm to 4.0 mm.

The device is readily adaptable to provide any desired protrusion (or even retrusion if required) merely by sizing the device with the gap "G" corresponding to the desired adjustment. "G" is provided by the arrangement of the holes 130*a–f* in the holder 100. In the preferred embodiment, to provide a different gap, only a different holder 100 need be employed; the upper and lower mouthpiece portions need not be changed.

It may be desirable that an appropriate size and/or offset may be selectable by a professional, such as the person's dentist, in order to accommodate an individual's particular mouth size and lower mandible adjustment needs. For example, in those individuals having a forwardly positioned lower jaw, that is a Class III position where the lower anteriors are already positioned in front of the upper anteriors, protrusion may not be advisable. A small or zero offset may be preferred but still effective for such persons.

In any case, persons with Class III jaw positions or other mouth conditions such as gingivitis, TMJ disease, periodontal disease or the like should be advised to consult a dental professional. Similarly, persons with physical conditions such as sleep apnea, high blood pressure, history of heart attack or angina should be advised to consult a physician.

Also, it is possible that merely preventing retrusion may be sufficient in certain individuals to reduce or eliminate the noise of snoring. The oral appliance of FIGS. 24–27 may be pre-assembled and then fitted in the assembled condition. Preferably, a simple handle comprising a spacer wedge within airway 72 would be implemented to hold the appliance 70 during heating and/or ensuring the integrity of the airway 72. The oral appliance 70 could be fitted and when worn would prevent retrusion of the lower jaw. The lower mouthpiece portion 30, being fitted to the lower teeth, provides comfort because retention forces are spread out over as large an area as possible rather than being concentrated in a single location.

Alternately, if no protrusion were to be required, the oral appliance 70 may be constructed from a one-piece design, preferably with a single hard plastic inner core piece (ramped on both sides) about which the pliable and conformable soft plastic body is formed. The appliance may also be constructed entirely of Elvax ® without an inner core piece. Even if protrusion were desired, fitting instructions may include having the dentist or other professional (or even the user) advance the lower jaw during the fitting process by guiding the person's lower jaw into a desired protruded position. In another embodiment, the lower mouthpiece portion 30 may be provided with a ramp which, during the fitting process, would urge the lower teeth forward to produce a desired protrusion of the lower mandible.

As previously described, the preferred construction of the pliable plastic material of the outer material of the mouthpiece portion 20, a soft, pliable plastic material which softens upon heating in hot water or other heating device such as a microwave oven but firms up and provides a soft comfortable fit when cooled. The preferred material is sold under the trade name Elvax 250 which is a plastic mix containing approximately 28% vinyl acetate available from DuPont Corporation and is commonly used for constructing mouthpieces. A less dense, softer material might be more comfortable, but may create difficulty in heating and handling. A more dense, harder material may create difficulty in the desired teeth "bottoming out" on the internal core piece 50.

Alternate mechanisms may be employed to produce the desired offset protrusion. For example, the applicator handle 100 may have ridges or a sawtooth design which corresponds to respective ridges or sawtooth configuration in the core piece 50 of the respective upper and lower mouthpiece portions 20, 30. When the applicator 100 is removed, a desired new position of the upper mouthpiece portion 20 relative to the lower mouthpiece portion 30 may be selected by repositioning the locking of the ridges or sawtooth configurations in the mouthpiece portions 20, 30. Such a design may permit custom adjustment of the protrusion by varying the offset during fitting process.

In yet another embodiment, the connection mechanism between the mouthpiece portions 20, 30 may be suitable connector element such as plastic or stainless screws or staples.

In another embodiment, an applicator may be provided with stainless or plastic screws (or such other advancement mechanism) in the posterior end of each leg which advances the lower mouthpiece portion relative to the upper mouthpiece portion by turning the screw to create the desired protrusion of the lower jaw. An advantage of this embodiment is that the device would be custom adjustable for the amount of protrusion between the range of, for example, 0.0 mm to 4.0 mm. This embodiment would not require an applicator/holder.

In another alternative embodiment, the appliance may comprise upper and lower mouthpiece portions which are interconnected in a sawtooth or ridge pattern with the ridges or sawtooth pattern in the upper mouthpiece portion mating with the corresponding pattern in the lower mouthpiece portion. After fitting, the upper and lower mouthpiece portions would be separated from each other and then repositioned using a suitable reference point or marking on the units to correspond the desired protrusion amount. Once repositioned, the upper and lower mouthpiece portions would be interconnected by a suitable mechanism such as a steel or plastic screw, staple, or other interconnection device.

Thus, an oral appliance and method for reducing the noise of snoring have been shown and described. Thus, certain examples and advantages have been disclosed. Further advantages and modifications may become obvious to one skilled in the art from the disclosures herein. The inventor therefor is not to be limited except in the spirit of the claims that follow.

What is claimed is:

1. An oral appliance for reducing snoring comprising:
   an upper mouthpiece portion having a rigid structural core and a relatively soft impression tray portion which may be conformed to fit a person's upper teeth;
   a lower mouthpiece portion having a rigid structural core and a relatively soft impression tray portion which may be conformed to fit the person's lower teeth;
   a holder element to which the upper and lower mouthpiece portions are attachable so as to position the upper mouthpiece portion at a slight forward offset relative to the lower mouthpiece portion, the upper and lower mouthpiece portions being conformed to fit the person's respective upper teeth and lower teeth while being attached to the holder element, wherein once the upper and lower mouthpiece portions are conformed, they are detachable from the holder element and reattachable to each other without the offset.

2. An oral appliance according to claim 1 wherein the upper mouthpiece portion and the lower mouthpiece portion are of identical configuration.

3. An oral appliance according to claim 1 wherein the upper mouthpiece portion and the lower mouthpiece portion are interchangeable.

4. An oral appliance according to claim 1 wherein the forward offset is approximately 3.0 mm.

5. An oral appliance according to claim 1 wherein the forward offset is in the order of 2.0 mm to 4.0 mm.

6. An oral appliance according to claim 1 wherein each rigid structural core of the upper and lower mouthpiece portions comprises a flat U-shaped member having a plurality of protruding connector elements and a plurality of holes formed therein.

7. An oral appliance according to claim 1 wherein the rigid structural core is constructed from a stiff plastic material which holds its shape during a heating process and the impression tray portion is constructed from a plastic material which softens and becomes pliable during the heating process to allow teeth impression to be made and which upon cooling retains its conformed shape and softness.

8. An oral appliance according to claim 1 wherein the impression tray portion is constructed from a plastic mix containing vinyl acetate material which softens and becomes pliable during the heating process to allow teeth impression to be made and upon cooling retains its conformed shape and softness and wherein the rigid structural core is constructed from a stiff plastic material.

9. An oral appliance comprising:
   an upper mouthpiece portion having a relatively soft impression tray portion which may be conformed to fit a person's maxillary teeth,
   a lower mouthpiece portion having relatively soft impression tray portion which may be conformed to fit the person's mandibular teeth;
   connector means for connecting the upper mouthpiece portion to the lower mouthpiece portion, said connector means having a plurality of attachment positions permitting the upper mouthpiece portion to be attached to the lower mouthpiece at different positions.

10. An oral appliance according to claim 9 wherein the an upper mouthpiece portion includes a rigid structural core to which the impression tray portion is attached and the upper mouthpiece portion includes a rigid structural core to which the impression tray portion is attached.

11. An oral appliance according to claim 9 further comprising adjustment means for adjusting position of the lower mouthpiece portion forward relative to the upper mouthpiece portion.

12. An oral appliance according to claim 9 wherein the upper mouthpiece portion and the lower mouthpiece portion are identical.

13. An oral appliance according to claim 9 further comprising
   attachment means for detachably connecting the upper mouthpiece portion to the lower mouthpiece portion with a desired forward offset of the upper mouthpiece portion relative to the lower mouthpiece portion and
   reattachment means for connecting the upper mouthpiece portion directly to the lower mouthpiece portion without the forward offset once the upper and lower mouthpiece portions are conformed.

14. An oral appliance according to claim 13 wherein the attachment means comprises a holder element to which the upper and lower mouthpiece portions are attachable so as to position the upper mouthpiece portion at a slight forward offset relative to the lower mouthpiece portion.

15. An oral appliance according to claim 9 wherein the the upper and lower mouthpiece portions are U-shaped with a center curved section and two rearwardly extending leg portions with each impression tray having a guide ramp in the center curved section for urging the user's teeth forward when the upper and lower mouthpiece portions are being conformed.

16. A method of constructing an oral appliance for a user's mouth, comprising the steps of
   connecting a first mouthpiece portion to one side of a relatively thin and flat holder element;
   connecting a second mouthpiece portion to the other side of the holder element with a desired offset relative to the first mouthpiece portion;
   conforming the first mouthpiece portion to the upper teeth of the user's mouth and the second mouthpiece portion to the lower teeth of the user's mouth;
   removing the first and second mouthpiece portions from the holder element;
   reattaching the first mouthpiece portion to the second mouthpiece portion without the offset.

17. A method of constructing an oral appliance according to claim 16 wherein the step of conforming the first and second mouthpiece portions comprises heating the first and second mouthpiece portions with a suitable heating mechanism, removing the first and second mouthpiece portions from the heating mechanism, inserting the first and second mouthpiece portions into the user's mouth, biting down into the first and second mouthpiece portions and removing them from the user's mouth.

18. A method of constructing an oral appliance according to claim 16 further comprising the step of selecting the desired offset to be in the order of three millimeters.

19. A method of constructing an oral appliance for a person's mouth, comprising the steps of
   assembling a first mouthpiece portion proximate to a second mouthpiece portion in an assembled condition;
   while in the assembled condition, conforming the first mouthpiece portion to the upper teeth of the user's mouth and the second mouthpiece portion to the lower teeth of the person's mouth;
   adjusting the position of the second mouthpiece portion forward relative to the first mouthpiece portion by a desired adjustment amount;
   securing the first mouthpiece portion to the second mouthpiece portion in the adjusted relative position.

20. A method of constructing an oral appliance according to claim 19 wherein the step of adjusting comprises
   before the conforming step, connecting the first mouthpiece portion to one side of a relatively thin and flat holder element and connecting a second mouthpiece portion to the other side of the holder element with an offset relative to the first mouthpiece portion equal to the desired adjustment amount and
   after the conforming step, removing the first and second mouthpiece portions from the holder element and reattaching the first mouthpiece portion to the second mouthpiece portion without the offset.

* * * * *